US 6,447,991 B1
(12) United States Patent
Daitch et al.

(10) Patent No.: US 6,447,991 B1
(45) Date of Patent: Sep. 10, 2002

(54) SMART AEROGEL

(76) Inventors: Charles E. Daitch, 1115 5$^{th}$ St., Charlottesville, VA (US) 22902; Jack S. Brenizer, Jr., 525 Shanelly Dr., Port Matilda, PA (US) 16870; Bouvard Hosticka, 1314 Rose Hill Dr., Charlottesville, VA (US) 22903; L. Roger Mason, Jr., 248 N. Columbus St., Arlington, VA (US) 22203; Pamela N. Norris, 1509 Still Meadow Cove, Charlottesville, VA (US) 22901; Ming Luo, 1659 Crossgate Dr., Vestavia, AL (US) 35216; Lawrence J. DeLucas, 2739 Altadena Rd., Birmingham, AL (US) 35243

( * ) Notice: Subject to any disclaimer, the term of this patent is extended or adjusted under 35 U.S.C. 154(b) by 0 days.

(21) Appl. No.: 09/222,068

(22) Filed: Dec. 29, 1998

Related U.S. Application Data

(60) Provisional application No. 60/070,279, filed on Dec. 31, 1997, and provisional application No. 60/066,592, filed on Nov. 26, 1997.

(51) Int. Cl.$^7$ .......................... C12Q 7/70; G01N 33/552
(52) U.S. Cl. ............................ 435/5; 435/7.1; 436/501; 436/527
(58) Field of Search .................. 435/5, 7.32; 436/501, 436/518, 527, 535

(56) References Cited

U.S. PATENT DOCUMENTS 5,360,572 A * 11/1994 Hotaling et al. ......... 252/181.6
5,767,167 A * 6/1998 Ferry .......................... 521/64
5,851,395 A * 12/1998 Kawase et al. ......... 210/500.27
6,022,748 A * 2/2000 Charych et al. ............ 436/527

OTHER PUBLICATIONS

Caruana C.M., Chemical Engineering Progress:11–17, Jun. 1995.*

* cited by examiner

Primary Examiner—Anthony C. Caputa
Assistant Examiner—Brenda G. Brumback
(74) Attorney, Agent, or Firm—John E. Wagner; Sam Bernardo

(57) ABSTRACT

Smart aerogel, an aerogel material doped with special bioaffinity compounds to providing means of unique collection, detection and identification of bioaerosols, including bacteria, viruses, toxins, and other bioaerosols. Aerogels, extremely low density and highly porous materials with a complex pore structure, are used as an intelligent detection material by incorporating specific bioaffinity pharmaceuticals directly into the matrix. The complex pore structure contains micropores, mesopores, and macropores in an open pore structure. The opening pore structure of the aerogel is used to create docking sites by linking high affinity pharmaceuticals that specifically bind only to certain bioaerosols. The high internal surface area of the aerogel and the extremely low density provides abundant receptor sites per unit mesopore for a high bioaerosol-receptor interaction, yet in a manner which will reduce possible damage and destruction to the bioaerosols captured.

20 Claims, 10 Drawing Sheets

Sialic acid → Aerogel Bulk View

Pore Size < 100 nm        Pore Size > 100 nm

Standard Recipe: ~ 0.1 μm
TetraEthylOrthoSilicate (TEOS)
Ethanol
$H_2O$
Two Step Acid-Base Catalysis Macro Pore Recipe: ~ 2 μm
TetraMethylOrthoSilicate (TMOS)
FormAmide
$H_2O$
$HNO_3$ (Acid Catalysis)

FIGURE 13

```
100
 90
 80
 70
 60
 50
 40
 30
 20
 10
  0
     Virus+    Aerogel    Sialoside
              Control     Aerogel
```

Influenza virus in aqueous solution.

SMART AEROGEL

CROSS-REFERENCE TO RELATED APPLICATIONS

This non-provisional application is based upon provisional patent application serial No. 60/070,279 filed Dec. 31, 1997 entitled "Aerogel Environmental Sampler and Concentrator", and provisional patent application serial No. 60/066,592 filed Nov. 26, 1997, and now non-provisional patent application No. 09/199,979, filed Nov. 25, 1998, now U.S. Pat. No. 6,101,886, entitled "Aerogel Environmental Sampler and Concentrator", the contents of which are incorporated herein by reference.

U.S. GOVERNMENT SPONSORED RESEARCH/DEVELOPMENT

Work under which this invention was made was sponsored in part by the U.S. Government under the following contracts:

Defense Advanced Research Projects Agency, BAA 96-35 "Next Generation, Integrated Biosensor", Pacific-Sierra Research, University of Virginia, and University of Alabama, Birmingham, Period of Performance: March 97–September 99.

Defense Advanced Research Projects Agency, Counter-Proliferation Support Program, BAA 96-35 "Smart Aerogels for Biosensor Applications", Pacific-Sierra Research and University of Virginia, Period of Performance: March 97–September 99.

BACKGROUND OF THE INVENTION

1. Field of the Invention

Material and method for use in capturing and uniquely identifying bioaerosols, more particularly bioaerosol receptor doped aerogels.

2. Description of Related Arts

Bioaerosols, including bacteria, viruses, toxins, and other biological materials generally have particle sizes ranging from 0.01 to as large as 10 µm and can sometimes be harmful if contacted with animals and/or inhaled. Although some sensors now exist to detect bioaerosols, current technology lacks the capability to provide unique, sensitive, and rapid detection of particular bioaerosols. Due to the extent and speed at which airborne pathogens may be able to spread and infect, a new generation of biological sensors is needed. There, accordingly, remains a need for a biological sensor material that is adapted for use in efficient collection, rapid detection, specific identification, and near real-time reporting of the presence of certain bioaerosols.

SUMMARY OF THE INVENTION

The "smart aerogel" of the invention constitutes an aerogel combined with bio-affinity receptors that have unique affinities to specific bioaerosols. Aerogels, sometimes referred to as "solid smoke", are multifunctional materials with unique properties that the inventors put to use to enable their use as a collection, assay, and identification media. Aerogels have two major properties of interest: a complex pore structure (micro- and meso-pores) with discrete ranges from 2 nm to 100 nm, as well as a macro structure of over 100 nm, and a large internal surface area (~1500 m²/g) that can be coated with reactant compounds. These different properties can be independently controlled during synthesis. Aerogel is manufactured into the advanced "smart aerogel" sensor media of the invention by linking reactant bio-affinity compounds to the internal matrix of the aerogel to create "docking" sites. Thereafter, any bioaerosols, including airborne pathogens impinging on the smart aerogel will be in contact with and preferably specifically bond to the receptor and thus selectively attach to the aerogel.

After a particular bioaerosol is captured in the smart aerogel, the smart aerogel can be sprayed with a mist of water or other fluids. This dissolves the smart aerogel and the captured bioaerosol into a small amount of solution that can then be analyzed. A device and means for accomplishing this is disclosed in non-provisional patent application No. 09/199,979, filed Nov. 25, 1998, entitled "Aerogel Environmental Sampler and Concentrator".

The bioaffinity compounds have a high selectivity and affinity for specified compounds, while the aerogel has a complex pore structure and extremely large internal surface area that renders a highly efficient, lightweight collection media. Combining the bioaffinity compounds with aerogels essentially produces a powerful "sponge" that will only absorb the specified bioaerosol. By providing a number of smart aerogels doped with one or more bio-affinity compounds, an air sample can be checked for a number of suspected bioaerosols.

BRIEF DESCRIPTION OF THE DRAWINGS

FIG. 13 compares free virus of solution for a virus solution, an aerogel control, and the sioloside aerogel of the invention to illustrate the selective uptake by the sioloside aerogel of the influenza virus.

DISCUSSION OF THE PREFERRED EMBODIMENT

1. Synthesis of Aerogel

Figure 1:
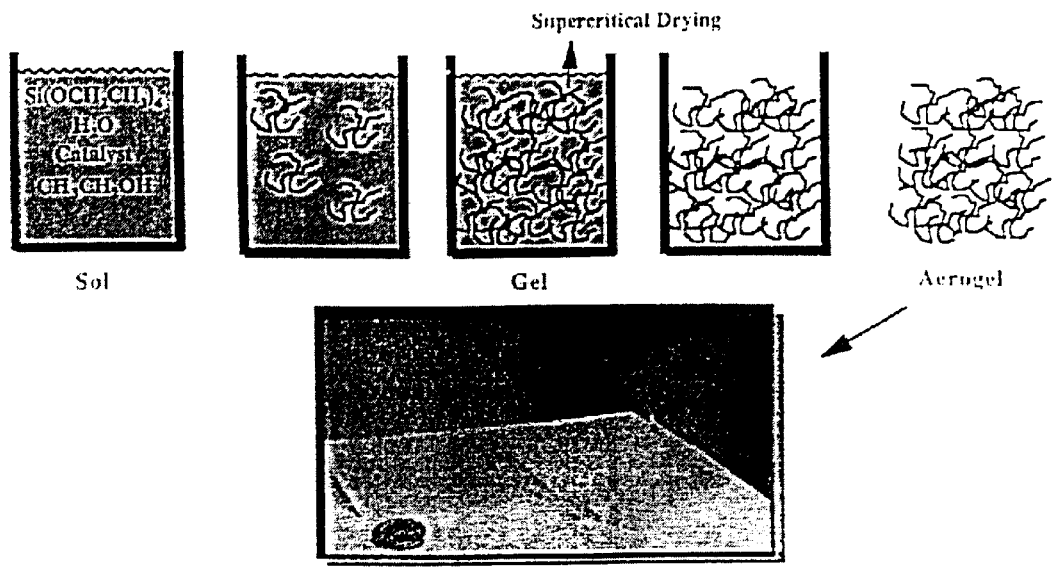
FIG. 1 shows the prior art aerogel synthesis process illustrating the sol-gel chemistry and supercritical drying that result in this low-density, high-porosity material.

One prior art method of regular (non-doped) aerogel production is the sol-gel process where a solution of silicate monomer (sol) undergoes polymerization to a gel, as shown in FIG. 1. Specifically, an ethanol solution of tetraethoxysilane $Si(OCH_2CH_3)_4$ in the presence of water, ethanol, and catalyst, undergoes partial hydrolysis and a condensation reaction to form a sol (a colloidal dispersion of particles in liquid). As the process of polymerization continues, a solid silicate network separates out of the solution (gel point). The solid is still "soaking" in the ethanol solution; this biphasic system is usually referred to as the alcogel. Subsequent removal of the liquid phase from the alcogel by supercritical drying, results in a low density, highly porous silica aerogel. The processes of forming aerogels are well-known.

Figure 2A:
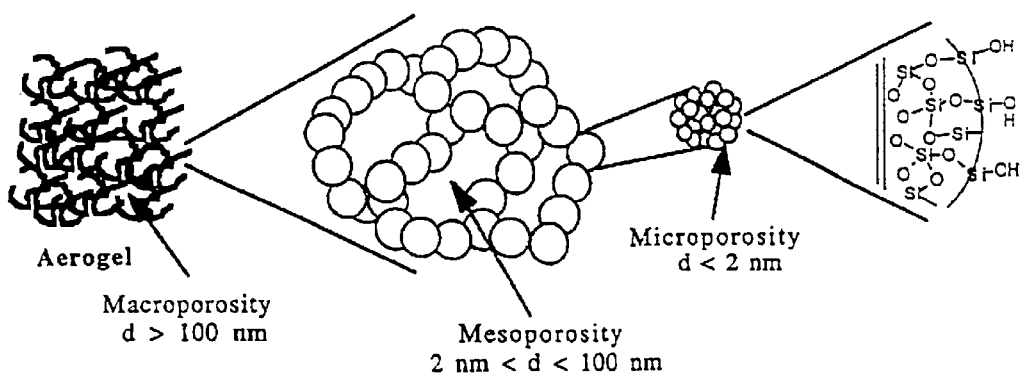
FIG. 2A shows complex aerogel pore structure consisting of a micro-, meso-, and macro-porosity.

FIG. 2 shows the three regimes of pore size that evolve during polymerization: micropores (<2 nm), mesopores (2 nm–100 nm), and macropores (>100 nm). Statistical control over the evolution of pore size can be accomplished by varying the reaction conditions. These statistical control states show that all three pore regimes are always present; however, one regime may be favored over the others. Reaction conditions yield control over pore size and include pH, solvent, temperature, hydrolysis ratio, and monomer concentration. Further discussion of how pore size can be controlled is set forth in the section below on pore engineering.

2. Doping the Aerogel

Doping refers to the process of adding a substance to the aerogel matrix. The surface of the silica aerogel pores is covered with silanol (SiOH) groups shown in FIGS. 2A and 2B, which give the aerogel its characteristic pore structure and hydrophilic nature. The surface silanol groups can be utilized for attachment of specified molecules (dopants) via hydrogen bonding, ionic bonding, or covalent bonding as illustrated in FIG. 3. It has been found that covalent bonding results in the most useful bonds.

Figure 4:
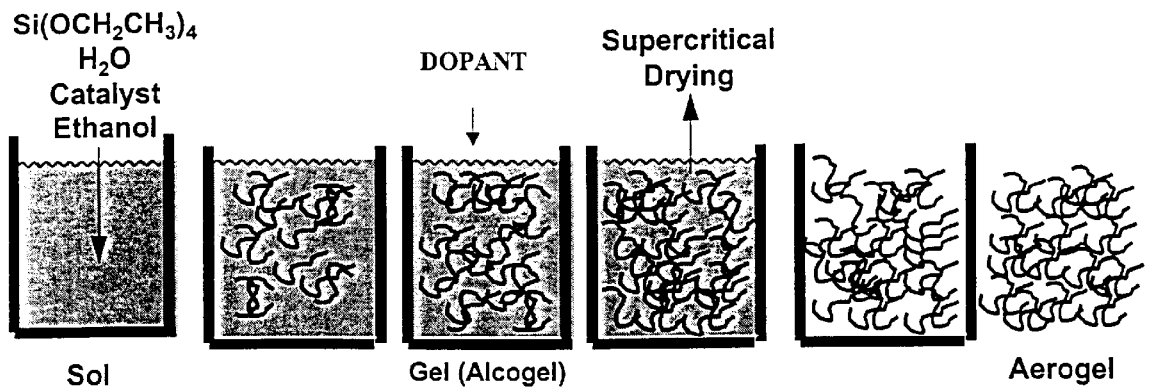
FIG. 4 is a schematic illustration of the process of incorporating bio-affinity compounds (dopants) directly into the aerogel pore matrix during synthesis.

The modified sol-gel process for incorporating dopants is shown in FIG. 4. Dopants are added at the alcogel stage and allowed to react with the surface silanols. Subsequent washing stages, followed by supercritical extraction, will result in a surface modified "doped" aerogel. The smart aerogels of the invention consist of a silica aerogel matrix doped with a high bio-affinity receptor drug. The first model used to test the feasibility of doping aerogel with high bio-affinity receptors for bioaerosols is for sialic acid directed toward the influenza virus. This virus is an envelope virus that probably infects hundreds of millions of people each year. There are two major surface glycoproteins (hemagglutinin and neuraminidase), that are the targets for the high affinity ligand design. Hemagglutinin is a protein responsible for viral attachment to the host cell through interactions with sialic acid residues located on the host cell's surface. Neuraminidase is responsible for viral release from the host cell and subsequent spreading of infection after viral penetration and multiplication. Hemagglutinin is the more abundant surface protein (90%) and plays a critical function in viral adhesion to the host cell. The structure of the influenza neuraminidase was initially determined by scientists who are currently designing drugs for both of these influenza surface proteins. (See Longman, R. *In Vivo* 1994, 5,23–31.)

Figure 5:
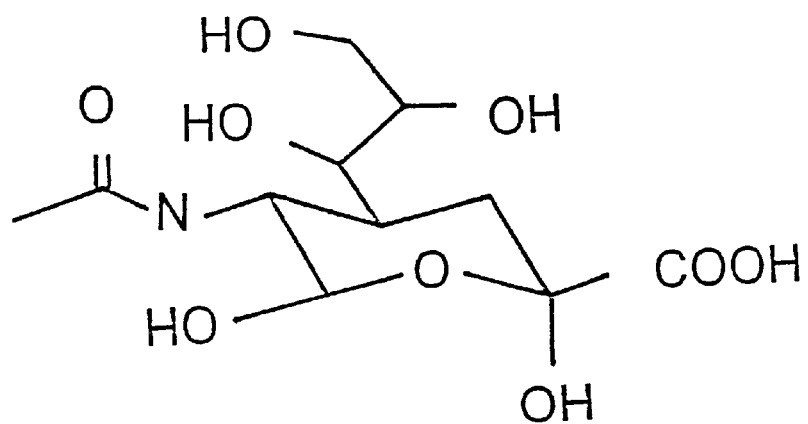
FIG. 5 shows the chemical structure of sialic acid.

Studies were conducted using the bio-affinity drug, sialic acid, shown in FIG. 5. As stated earlier, sialic acid is a molecular residue that binds to the glycoprotein hemagglutinin on the surface of the flu virus. It was chosen as a model for a biochemical aerosol (BA) specific drug because sialic acid is readily accessible, relatively inexpensive, and has a molecular weight and chemical functionality similar to other BA specific drugs. In addition, performance testing of aerogels doped with sialic acid can be accomplished with an inactive flu virus; thus, making these studies less hazardous compared to BA performance testing.

Three different modes for attachment of a molecular species (i.e., sialic acid) to the aerogel matrix have been discussed: hydrogen bonding, ionic bonding, and covalent bonding. For the purpose of BA sensor applications, covalent bonding stands out as the most efficient mode of attachment. To understand why, the fundamental principles of molecular recognition must be understood, which is the conceptual basis for the proposed BA sensor. In its simplest form, Equation 1 shows that molecular recognition involves the association of a receptor (A) and a substrate (B) to form the complex (AB). In Equation 2, $K_o$ is the binding constant that represents the ratio of the concentrations of products to reactants at thermodynamic equilibrium. A large $K_o$ represents a large binding constant signifying that the receptor has a high affinity for the substrate.

$$A + B \stackrel{K_0}{\rightleftharpoons} AB \quad \text{Eq. 1}$$

$$K_0 = \frac{[AB]}{[A][B]} \quad \text{Eq. 2}$$

Figure 6:
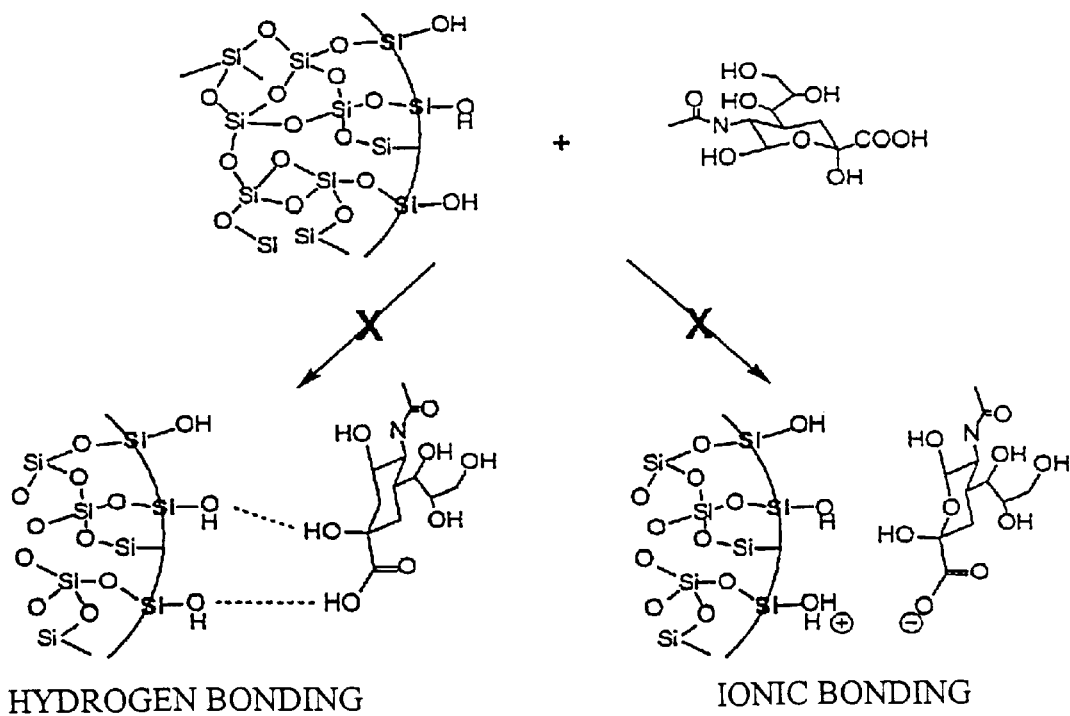
FIG. 6 illustrates the ionic and hydrogen bonding modes that prohibit functional group interaction.

In the case of biological systems, the receptor is a proteinacious active site, which forms a three dimensional pocket that "exactly" fits the substrate, and is sometimes referred to as the lock and key interaction. For the interaction to be efficient, the substrate must be able to utilize its chemical functional groups when binding to the pathogen active site. It is for this reason that hydrogen bonding and ionic bonding may hinder the proper interaction as shown in FIG. 6. The hydrogen and ionic bonding modes of attachment utilize the drug's chemical functional groups to actively "bond" to the aerogel surface, and thus, prevent these functional groups from interacting with the pathogen active site.

Figure 7:
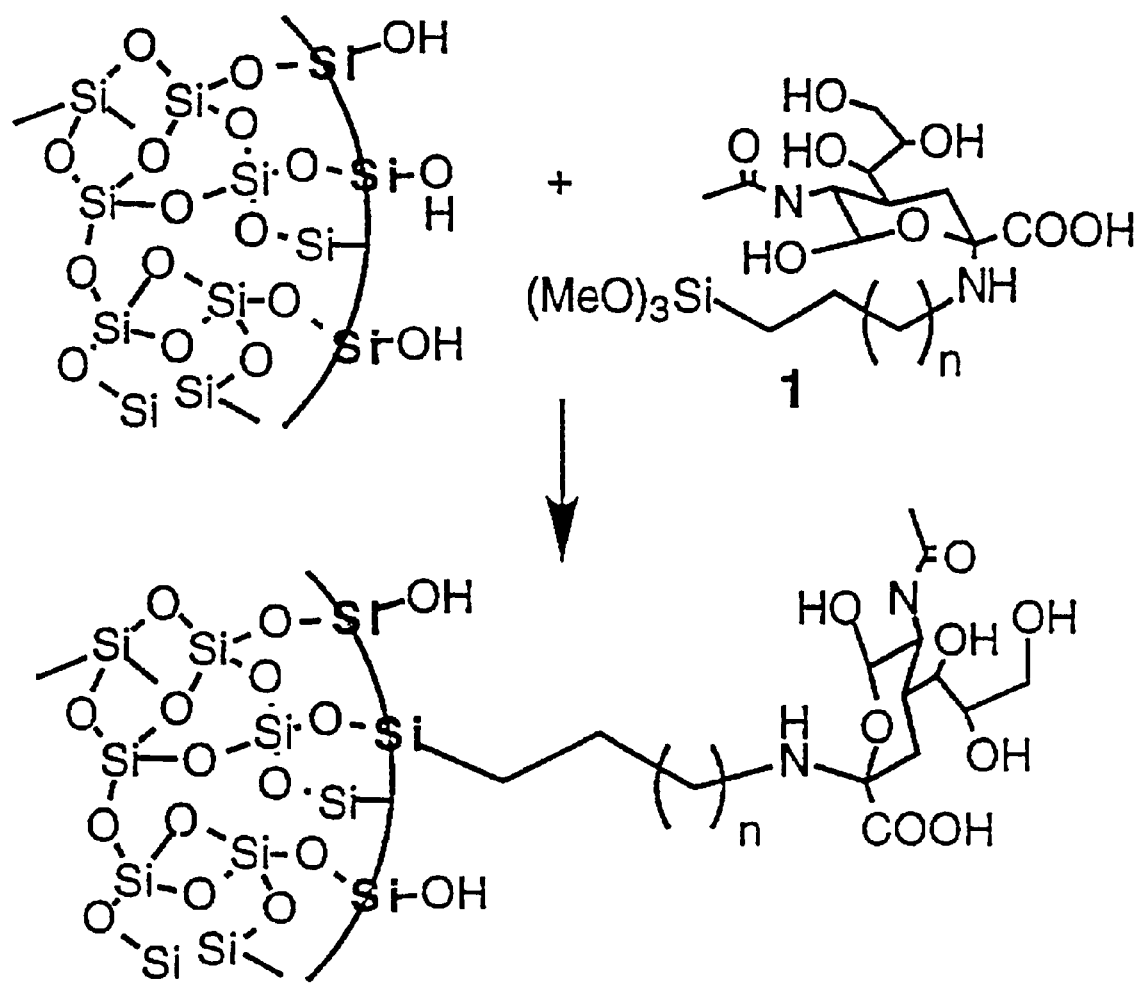
FIG. 7 depicts chemical bonding of the aerogel surface with a polymerizable pendant arm.

One way to circumvent this problem is to covalently attach the receptor drug via a polymerizable pendant arm to the aerogel surface as shown in FIG. 7. This way, the receptor drug has more degrees of freedom; thus, presents itself in an efficient manner to the active site of the pathogen. The modified drug, as shown in FIG. 7 is synthesized. The sol-gel process remains unchanged from the sol to gel steps. At the gel point, an ethanol solution of the bio-affinity drug (dopant) will be added. The trimethoxysilane functional group of the bioaffinity drug will react with the pore surface silanol groups; thus, attaching the receptor to the matrix. Subsequent washing stages, followed by supercritical extraction, results in a surface modified "doped" smart aerogel. As additional bio-affinity drugs specific for the desired bioaerosols become available, they will be attached to aerogels in the same fashion as sialic acid.

Figure 8:
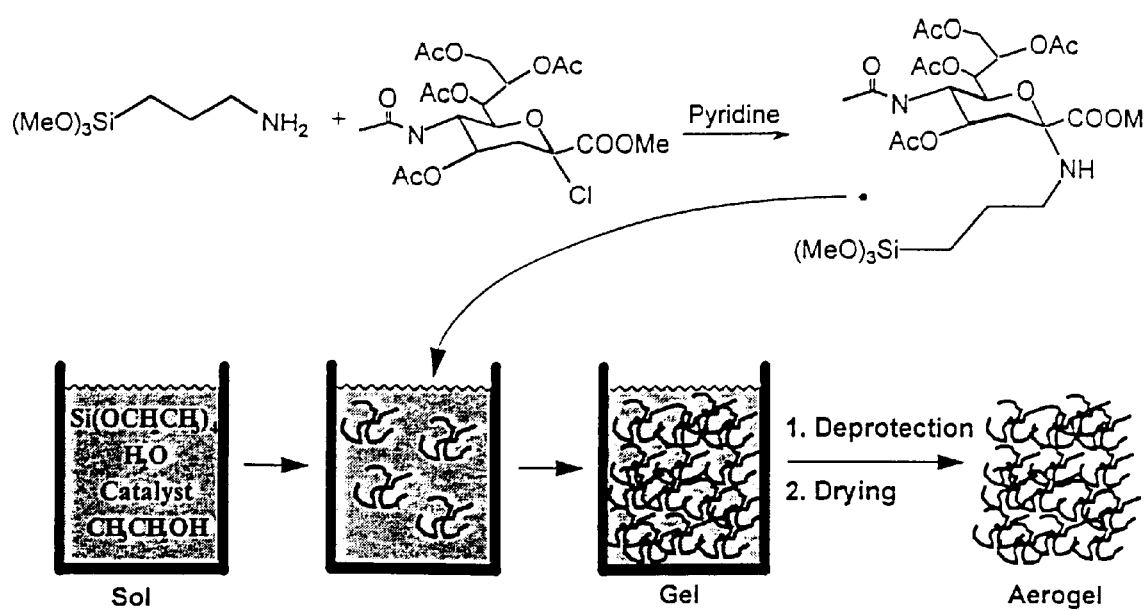
FIG. 8 illustrates one method of attaching a pendant arm to form sialoside and incorporating it into the aerogel to form the smart aerogel sialoside aerogel.

The inventors have found that it is preferable to protect the sialic acid before polymerizing it with the pendant arm. Turning to FIG. 8, to form the smart aerogel sialoside aerogel, aminopropyl trimethoxysiloxane is added to choroactivated and acetate protected sialic acid in pyridine to form the polymerized and protected sialic acid derivative. This derivative is then added to the sol at or just before the gel stage. Thereafter, the acetate protected sialic acid is deprotected and is supercritically dried to form the sialoside aerogel.

3. Pore Engineering

Figure 9:
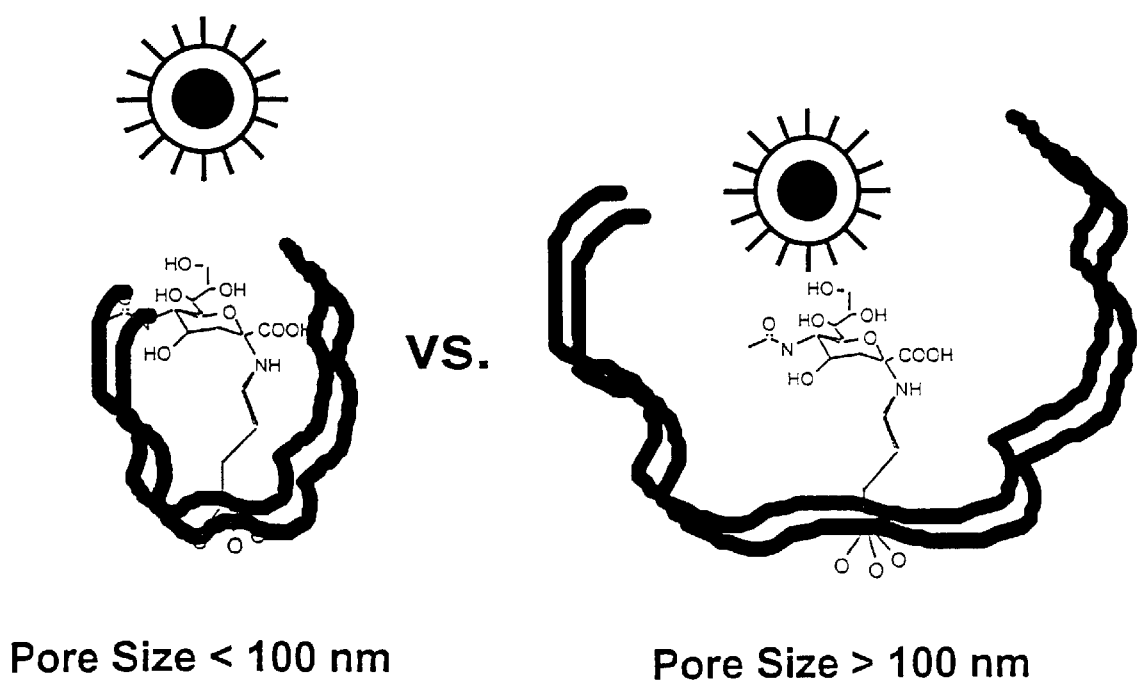
FIG. 9 is a diagrammatic illustration comparing pore sizes of aerogels doped with sialic acid to accommodate an influenza virus.
Figure 10:
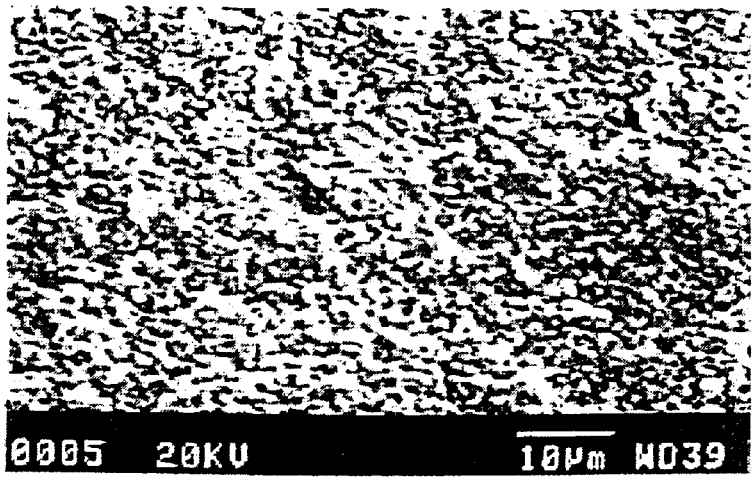
FIG. 10 is a scanning electron microscope view of a standard recipe aerogel with pore sizes of about ~0.1 µm.
Figure 11:
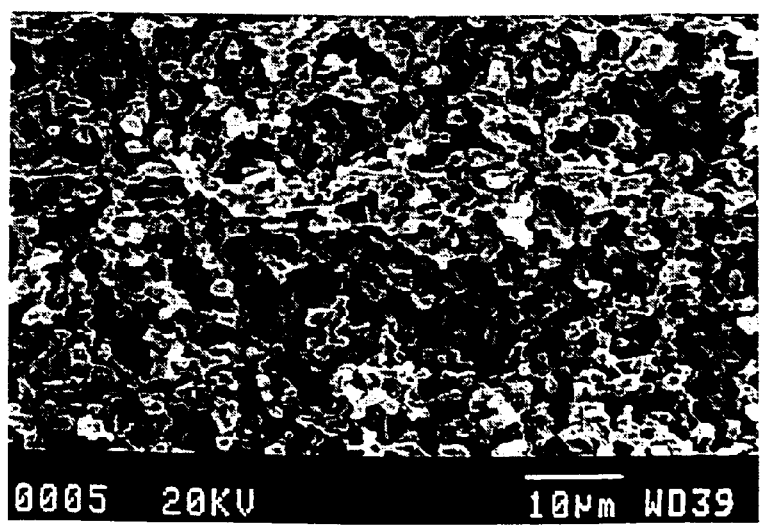
FIG. 11 is a scanning electron microscope view of a macro-pore recipe for aerogel with a pore size of about ~2 µm.

A major goal of the invention is to engineer aerogel pores sized to accommodate the bioaerosols intended to be captured. See FIG. 9, which diagrammatically illustrates the relationship between the size of the bioaerosol and the pore size, in the case of the influenza virus. FIGS. 10 and 11 are electron microscope images showing, respectively, a standard recipe aerogel with a pore size of about about ~0.1 $\mu$m, and a macro-pore recipe for aerogel with a pore size of about ~2 $\mu$m.

As noted above, control over the pore size of the aerogel can be accomplished by various methods. By adjusting reaction conditions of the sol (e.g., the pH (catalyst is acid or base), type of solvent, temperature, hydrolysis ratio $[H_2O]/[Si(OCH_2CH_3)_4]$, and the degree of dilution of $Si(OCH_2CH_3)_4$, the control over the mesopore range (2 to 100 nm) pore size range can be controlled. The macropore range (>100 nm) can be controlled by adjusting template pore sizing factors, including surfactants, latex microspheres, and multicomponent phase separation.

As stated above, the aerogel pore sizes can be described as follows:

| | | |
|---|---|---|
| Micropore | = | <2 nm |
| Mesopore | = | 2 nm > d > 100 nm |
| Macropore | = | >100 nm |

Control over pore sizing is as follows:

| | | |
|---|---|---|
| Micropore | = | no control |
| Mesopore | = | by reaction conditions |
| Macropore | = | by pore templating |

In general, the various bioaerosols have the following size ranges:

| | | |
|---|---|---|
| Bacteria, e.g. anthrax | = | 0.8 ~ 1 $\mu$m (800 ~ 1000 nm) |
| Rickettsia, e.g. Q-fever | = | 2 ~ 4 $\mu$m (200 ~ 4000 nm) |
| Viruses, e.g. VEE | = | 0.05 $\mu$m (50 nm) |
| Toxins, e.g. Botulism | = | 0.1 $\mu$m (10 nm) |

Given the foregoing, viruses and toxins fall within mesopore range, and therefore pore size can be engineered to ideal size by manipulating the reaction conditions. Bacteria and Rickettsia fall within the macropore range, and therefore the necessary pore size can be engineered by manipulating pore templating. Indeed, by correct pore engineering, the aerogel can be designed to lessen attachment, for example, of oversized bioaerosols to the receptors bonded to the interior surface of the pores. In this way, the selectability of the smart aerogel is enhanced and a greater percentage of the targeted bioaerosol than if the distribution of pore sizes is left to chance.

4. Characterization of the Bioaerogels

Next, the synthesized bioaerogels are characterized on both a systematic and component scale.

Figure 2B:
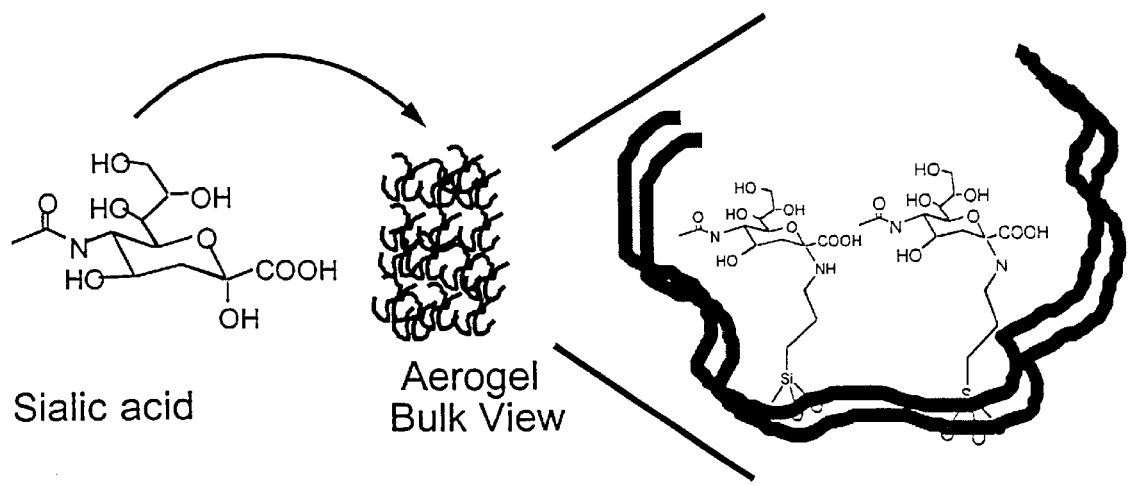
FIG. 2B diagrammatically illustrates sialic acid with a pendant arm incorporated into the aerogel to form the smart aerogel sialoside aerogel.
Figure 3:
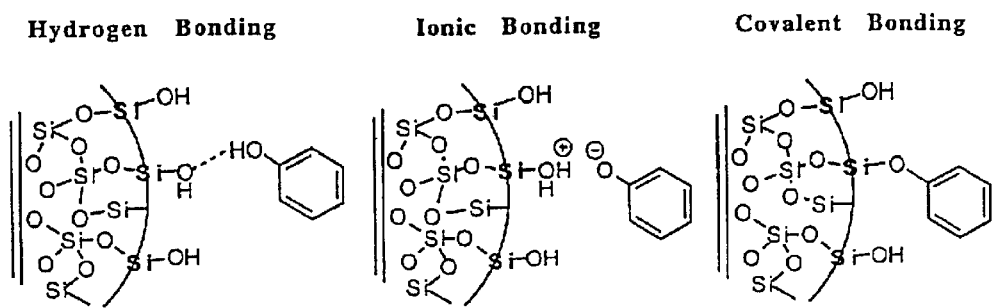
FIG. 3 shows potential chemical binding methods to incorporate the bio-affinity receptors into the aerogel matrix.

After the bio-affinity compounds are incorporated into the aerogel matrix, as shown in FIGS. 2B, 7, and 8 it is necessary to assess the influences of this process on both the aerogel nanostructure and the bio-affinity receptor compound. Specifically, characterization of the aerogel nanostructure will probe physical characteristics including density, surface area, porosity, pore size, and pore volume. Characterization of the doped bioaffinity drug will examine its covalent attachment (as opposed to non-covalent physical absorption) to the aerogel matrix. Non-covalent physical absorption is a secondary reaction, which can occur during the production process and can create problems such as drug leaching, reduced shelf life, and inefficient binding. Lastly, characterization will be performed to verify that the production process does not decompose the drug.

Sialic acid survives the harsh conditions of aerogel production. In an experiment to prove this, sialic acid was dissolved in ethanol and loaded into an autoclave. Liquid $CO_2$ was added to the mixture. The temperature of the mixture was raised to 45° C. and 87,700 Kg/m$^2$ (1250 psi) for three hours, after which the mixture was brought back to room temperature and pressure. The ethanol was removed by rotary evaporation, and $^1$H NMR spectra of the control and experimental batches were taken. The spectra were identical, indicating no damage to the sialic acid molecule.

Table 1 shows the primary characterization methods and the information obtained from each analysis. Methods 1–4 probe the bio-affinity drug. [1. Elemental Analysis (EA); 2. FT Infrared Spectrometry (FTIR); 3. Mass Spectrometry; and 4. Solid State Nuclear Magnetic Resonance Spectrometry (NMR)]. An aerogel doped with sialic acid, FIGS. 7 and 8, will be used as an example. Elemental analysis is a simple combustion reaction, which yields a percent composition of elemental carbon, hydrogen, nitrogen, and silicon in the final aerogel product. If for example, sialic acid is doped into the aerogel matrix at a 5% concentration (molar ratio), elemental analysis verifies the true concentration. FT infrared spectrometry (FTIR) examines molecular bond stretching and bending frequencies of the bioaffinity drug; sialic acid yields characteristic absorption frequencies consistent with a carbonyl functional group, an alcohol, and an amide. Mass spectrometry will provide secondary verification of drug incorporation. This type of analysis yields the molecular weights of ionized fragments in the aerogel matrix. A positive result shows a mass unit consistent with the molecular weight of the sialic acid. Solid state nuclear magnetic resonance (NMR) spectroscopy is the most important method of characterization. The analysis involves probing the bioaffinity drug's molecular connectivity to determine how the atoms in the drug are connected to each other and results in a spectrum of atom frequencies. A $^{13}$C NMR experiment involves analyzing the carbon resonances of a sample of sialic acid, which was not doped into the aerogel (control), and then analyzing the sialic acid resonances in the doped aerogel. $^{13}$C are ideal for this type of investigation because the aerogel matrix does not have any carbon; it is composed of silicon oxide, which will not interfere with the sialic acid carbon resonances. The carbon resonances of sialic acid should remain the same when doped into the aerogel; the spectrum will be identical to the control spectrum. Therefore, $^{13}$C NMR analysis provides verification that the sialic acid is incorporated into the aerogel matrix and does not decompose during the production process. $^{29}$Si NMR analysis of the sialic acid doped aerogel will provide quantitative data in conjunction with the elemental analysis. The silicon atom of the polymerizable arm will resonate at a different frequency than the silicon atoms of the aerogel matrix. These different silicon peaks can be integrated in the NMR spectrum, and the ratio of the areas will yield a percent concentration of the dopant in the aerogel matrix. Observation of the $^{13}$C and $^{29}$Si resonances of precursor bio-affinity drug, FIG. 7, in the aerogel matrix can unequivocally verify covalent attachment of the bio-affinity drug and that the drug's molecular integrity is maintained.

Methods 5–8, Table 1, [5. Mass and volume measurements; 6. Porosimeter; 7. Tunneling Electron Microscopy (TEM); and 8. Small Angle X-ray Scattering (SAXS)] will analyze the smart aerogel's physical characteristics. These parameters are important to measure because the success of the sensor relies on a highly lightweight, porous network to capture the pathogens. The measurements will provide a record of consistency for the aerogel characteristics from batch to batch. Density data will be obtained by determining the mass of an aerogel sample and dividing that by the volume (mg/m$^3$). Aerogel samples typically yield densities in the range of 5 mg/m$^3$ to 400 mg/m$^3$ (air has a density of 1 mg/m$^3$), which will fit in well for applications involving mounting on a micro unattended airborne vehicle (UAV).

Another important method of analysis to be used to determine the physical characteristics of the aerogel is porosimetry. The porosimeter measures surface area, porosity, pore size, and pore volume based on the absorption and desorption of gas (typically nitrogen) on the surface and in the pores of the aerogel. An imbalance of atomic forces on the surface of an evacuated solid attracts gas molecules. When these molecules collide with the surface, they either bounce off or are absorbed (become attached) onto the aerogel surface. The period of time a gas molecule absorbs on the surface of the aerogel depends on the energetics of the surface with which it collides: the physical and chemical nature of the sample and the gas, and the temperature of the sample. Adsorption is the concentration of gas molecules at the surface of the aerogel. When molecules leave the bulk of the gas to absorb onto the surface of a sample, the average number of molecules in the gas decreases; therefore, the pressure decreases. A pressure transducer detects this change in pressure. The analyzer determines the number of adsorbed molecules from the change in pressure, the temperature of the gas, and the volume of the container. It then automatically calculates surface area, porosity, pore size, and pore volume using the BET and BJH methods. (BET refers to the individuals Brunauer, Emmett, and Teller who developed the method to estimate the number of molecules required to cover the absorbant surface. BJH refers to the individuals Barrett, Joyner, and Halenda who developed computational methods used to determine pore sizes from equilibrium gas pressures.) The final two characterization methods will be used on a limited basis to provide secondary backup confirmation of pore size data obtained from the porosimeter. Tunneling electron microscopy (TEM) data is hard to interpret as the technique provides a two-dimensional projection of a three-dimensional structure. Small Angle X-ray Scattering (SAXS) circumvents this problem because X-ray scattering occurs throughout the material, and thus, yields information on ordered units in three dimensions, such as pore sizes. TEM and SAXS compliment each other and will be useful to characterize materials that show promise for first generation sensors.

5. Performance Engineering and Techniques

The criteria to judge smart aerogel performance are pathogen affinity and selectivity. Affinity refers to how "strong" of an interaction there is between the smart aerogel and the pathogen, and selectivity refers to the smart aerogel's ability to distinguish the specified pathogen from a sea of molecules present in the air. The goal of a biosensor is to have a high pathogen affinity and selectivity; this creates a sensor that can detect levels of pathogen that are not harmful to personnel and has a selectivity that minimizes background noise and false positives. There are two factors that will contribute to the smart aerogel's performance for discrete pathogens: 1) the bioaffinity drug, and 2) the aerogel matrix. The drug and aerogel matrix will be tested for their performance as separate entities, followed by performance studies as a single bioaerogel unit. This protocol will allow for a complete understanding of how each factor enhances or hinders the performance of the complete smart aerogel unit.

Pathogen affinity, $K_o$, is defined by the strength of the noncovalent molecular interactions between the receptor drug and pathogen (receptor and substrate). $K_o$ is represented in Equations 1 and 2 above, where the bioaffinity drug is represented by (A), and the pathogen is represented by (B). A large $K_o$ is equivalent to a high pathogen affinity. For example, the average association constant $K_o$ for a monovalent hapten and a divalent IgG antibody is $3.5 \times 10^5$ liters/mole. Bio-affinity drugs for BA pathogens with a $K_o$ in the range of $10^6$ to $10^9$ liters/mole will be developed. Studies will be performed utilizing a wide array of enzyme assays to measure pathogen affinity (relative thermodynamic concentrations). Selectivity will be monitored by running a binding assay consisting of the bioaffinity drug and the specified pathogen. Additionally, there will be nonspecific competing pathogens present. The assay will monitor the concentrations of specific pathogenic and nonspecific pathogenic substances in the sample chamber. A positive experiment (high selectivity) will be represented by a higher concentration of the specific pathogen bound to the bioaffinity drug versus the competing substances.

Next, performance studies on the smart aerogel will be executed. The smart aerogel performance is based on how efficiently the pores can accommodate the pathogen. There is an ideal pore size for the biosensor application where the pore is large enough to accommodate the specified pathogen. This kind of pore size engineering provides size exclusion selectivity, which further enhances the aerogel's performance. As discussed above, pore size can be varied by controlling the reaction conditions of the sol-gel process. Studies will be performed that probe the effects of varying the reaction conditions on the physical characteristics of the aerogel shown in Table 2. The physical characteristics of the aerogel will be characterized by methods described above. Knowledge of these effects will guide the pore engineering, such that the aerogel matrix can accommodate specified pathogens. The ability to tailor the properties of the smart aerogel matrix for a specific biological pathogen makes aerogel a very attractive material for sensor applications.

Figure 12:
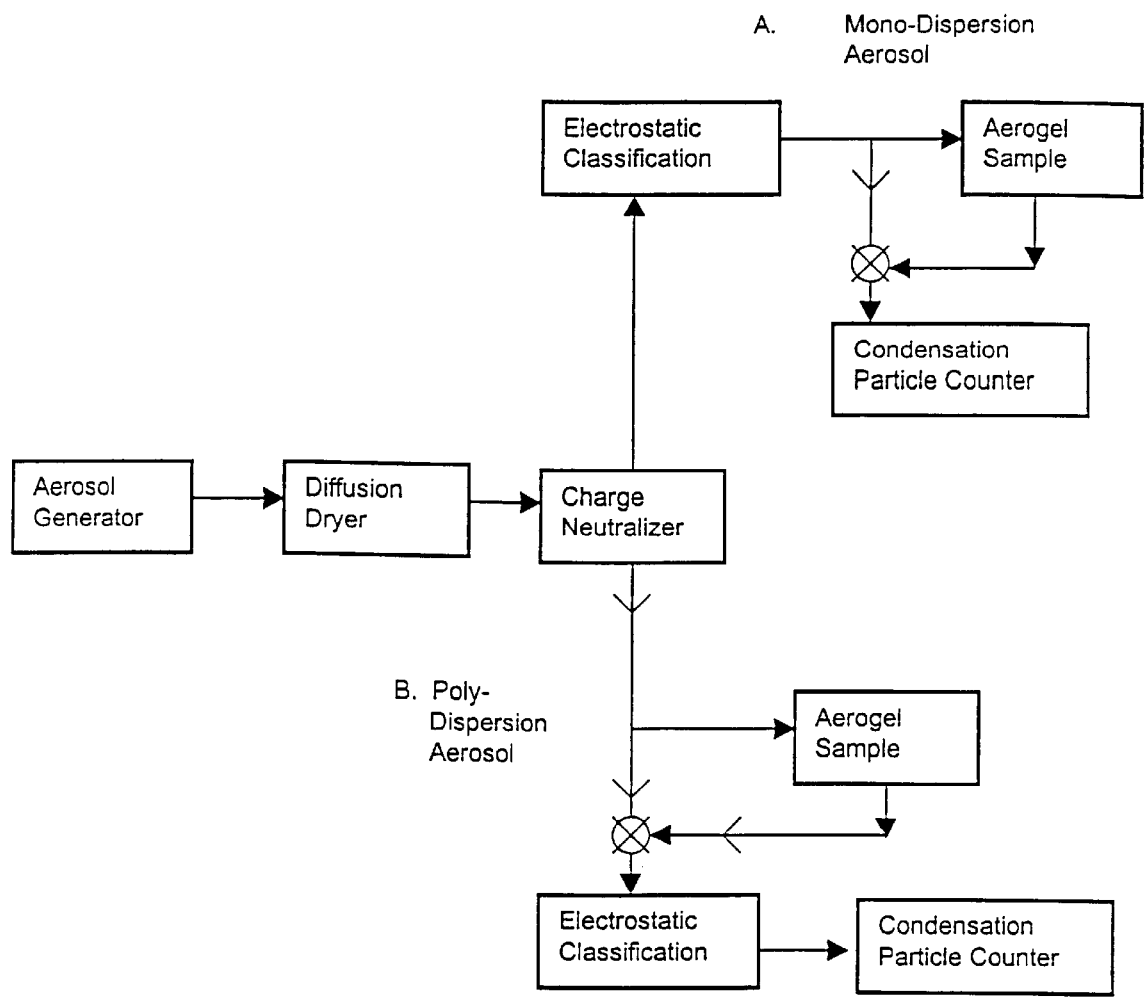
FIG. 12 is a block diagram of the aerosol testing apparatus, A) mono-dispersion aerosol testing, B) poly-dispersion aerosol testing.

After smart aerogels have been synthesized according to the parameters shown in Table 2, performance testing will be carried out with the apparatus shown in FIG. 12. The system generates an aerosol, which is passed through an aerogel sample, followed by detection using a particle counter. Two types of experiments can be performed with this type of system: (A) mono-dispersion testing or (B) poly-dispersion testing. Monodispersion testing generates a discrete size of aerosol, which is then passed through the smart aerogel sample, followed by detection. This type of experiment will test the smart aerogel's affinity for a certain size of aerosol. Poly-dispersion testing passes an aerosol containing a spectrum of particle sizes through the smart aerogel sample followed by particle size classification and detection. This type of experiment will test the aerogel's particle size selectivity.

Final performance testing will be executed with the doped aerogel sample, which is expected to provide exceptional performance by utilizing both the high affinity drug and the size exclusion properties of the smart aerogel's pores. Qualitative performance testing of the doped bioaerogel can be accomplished with the aerosol system, FIG. 12. Bioaerosols can be generated with an aqueous solution containing nonspecific biomolecules and the specified pathogen. After the bioaerosol has been passed through a smart aerogel sample, the sample will be taken out of the chamber and assayed through wet chemistry processes to determine how much and what kind of biomolecules the smart aerogel sample absorbed. A control experiment will be done with an undoped smart aerogel sample as a comparison. Positive results would include: 1) a greater concentration of the specified pathogen absorbed by the smart aerogel versus the nonspecific biomolecules, and 2) a greater concentration of specified pathogen absorbed versus the undoped aerogel.

The inventors have conducted studies which prove selective and enhanced binding of the influenza virus with the sialoside aerogel. FIG. 1 graphically displays an assay measurement of the amount of free virus (influenza) in an aqueous solution, with no aerogel, with a prior art undoped aerogel, and the sialoside aerogel. As shown, an aqueous solution of influenza virus at a concentration of about 95 will drop to about a concentration of about 62 when a regular aerogel is placed in the solution (indicating an uptake of about 33 by the undoped aerogel.) However, when the sialoside aerogel is placed in the viral solution, the virus count drops to about 33, indicating a virus uptake of about 68 out of a total of 95. This clearly indicates an enhanced uptake by the sialoside aerogel of the invention when compared to undoped aerogel.

6. Environmental Air Sampler Using Smart Aerogel for Biological Material Collection and Fluid Reduction The smart aerogel of the invention can be used in an environmental air sampler for bioaerosol collection and fluid reduction such as that disclosed in the co-pending U.S. patent application Ser. No. 09/199,979. Aerogel has been demonstrated as a forced flow filtration media that is extremely hygroscopic. Experimental and theoretical investigations demonstrated the capability to incorporate sample preparation compounds that enable the assay of biological pathogens using a time-of-flight mass spectrometer. The compounds, known as MALDI acids (Matrix Assisted Laser Desorption Ionization), were synthesized directly into the aerogel pore structure and did not cause interference in the time-of-flight assay.

As can be seen, bioaerosol receptor doped aerogels can thus be used as a material to selectively capture bioaerosols including bacteria, viruses, and toxins. While the example of doping an aerogel with sialic acid to form sialoside aerogel for the influenza virus was given, by selecting other dopants and by also engineering the appropriate pore sizes in the aerogel, smart aerogels to selectively collect other particular bioaerosols can be designed. In addition, a single sample of aerogel can be doped, if desired, with more than one different bioaerosol receptors so that the smart aerogel can be used to capture and detect the presence of more than one bioaerosol.

The drawings and the foregoing description are not intended to represent the only form of the invention in regard to the details of this construction and manner of operation. In fact, it will be evident to one skilled in the art that modifications and variations may be made without departing from the spirit and scope of the invention. Although specific terms have been employed, they are intended in generic and descriptive sense only and not for the purpose of limitation.

TABLE I

| | Characterization Method | Measurement Information |
|---|---|---|
| 1 | Elemental Analysis (EA) | Yields quantitative verification of drug incorporation in the aerogel matrix Obtained a percent composition (i.e., 5% dopant) |
| 2 | FT Infrared Spectrometry (FTIR) | Yields qualitative verification of drug incorporation and molecular integrity (drug remains intact) |
| 3 | Mass Spectrometry (MS) | Yields qualitative verification of drug incorporation |
| 4 | Solid State Nuclear Magnetic Resonance Spectroscopy (NMR) | $^{13}C$ analysis yields qualitative verification of drug incorporation and molecular structural integrity $^{29}Si$ analysis yields quantitative verification of drug incorporation and probes the extent of polymerization reaction |
| 5 | Mass and Volume Measurement | Evaluates material density |
| 6 | Porosimeter | Provides surface area, porosity, pore size distribution and pore volume data |
| 7 | Tunneling Electron Microscopy (TEM) | Provides cell/pore size information and morphology |
| 8 | Small Angle X-Ray Scattering (SAXS) | Evaluates mean pore size and fractal nature of aerogels |

TABLE 2

| | | Physical Characteristics | | | | |
|---|---|---|---|---|---|---|
| | Reaction Conditions | Density | Surface Area | Porosity | Pore Size | Pore Volume |
| 1 | pH | ● | ● | ● | ● | ● |
| 2 | Hydrolysis Ratio | ● | ● | ● | ● | ● |
| 3 | Monomer Concentration | ● | ● | ● | ● | ● |
| 4 | Doping | ● | ● | ● | ● | ● |

We claim:

1. A bioaerosol receptor doped aerogel for use in selectively capturing bioaerosols comprising an aerogel with a porous structure doped with a bioaerosol receptor for interaction with a biologically active site of the bioaerosol.

2. The bioaerosol receptor doped aerogel of claim 1 wherein the aerogel defines micropores, mesopores, and macropores, the micropores, mesopores, and macropores having interior surfaces, and wherein the bioaerosol receptors are bonded to at least interior surfaces of at least one of the micropores, mesopores, and macropores.

3. The bioaerosol receptor doped aerogel of claim 2, wherein the micropores are in the size range of less than about 2 nanometers, the mesopores are in the size range of between 2 nanometers and 100 nanometers, and macropores are in the size range of between about 100 nanometers and 10,000 nanometers.

4. The bioaerosol receptor doped aerogel of claim 2, wherein the bioaerosol receptors are covalently bonded to the interior surfaces of at least one of the micropores, mesopores, and macropores.

5. The bioaerosol doped aerogel of claim 2 wherein the bioaerosol receptor is modified to include a pendant arm, which pendant arm is adapted to covalently bond to the interior surface of the pores of the aerogel.

6. The bioaerosol receptor doped aerogel of claim 2, wherein the bioaerosol is the influenza virus, and the bioaerosol receptor is sialic acid.

7. The bioaerosol receptor doped aerogel of claim 6 wherein the sialic acid is covalently attached to the interior surface of the pores of the aerogel via a pendant arm.

8. The bioaerosol receptor doped aerogel of claim 2, wherein the aerogel is engineered so that an enhanced percentage of the pores with bonded bioaerosol receptors are sized to allow the targeted bioaerosols to at least partially enter the pores.

9. The bioaerosol receptor doped aerogel of claim 1, wherein the aerogel is doped with a single type of bioaerosol receptor.

10. The bioaerosol receptor doped aerogel of claim 1, wherein the aerogel is doped with more than one type of bioaerosol receptor.

11. A bioaerosol receptor doped aerogel for use in selectively capturing bioaerosols comprising an inorganic silica-based aerogel with a porous structure doped with a bioaerosol receptor for interaction with a biologically active site of the bioaerosol.

12. The bioaerosol receptor doped aerogel of claim 11 wherein the inorganic silica-based aerogel defines micropores, mesopores, and macropores, the micropores, mesopores, and macropores having interior surfaces, and wherein the bioaerosol receptors are bonded to at least interior surfaces of at least one of the micropores, mesopores, and macropores.

13. The bioaerosol receptor doped aerogel of claim 12 wherein the micropores are in the size range of less than about 2 nanometers, the mesopores are in the size range of between 2 nanometers and 100 nanometers, and macropores are in the size range of between about 100 nanometers and 10,000 nanometers.

14. The bioaerosol receptor doped aerogel of claim 12 wherein the bioaerosol receptors are covalently bonded to the interior surfaces of at least one of the micropores, mesopores, and macropores.

15. The bioaerosol receptor doped aerogel of claim 12 wherein the bioaerosol receptor is modified to include a pendant arm, which pendant arm is adapted to covalently bond to the interior surface of the pores of the inorganic silica-based aerogel.

16. The bioaerosol receptor doped aerogel of claim 12 wherein the bioaerosol is the influenza virus, and the bioaerosol receptor is sialic acid.

17. The bioaerosol receptor doped aerogel of claim 16 wherein the sialic acid is covalently attached to the interior surface of the pores of the aerogel via a pendant arm.

18. The bioaerosol receptor doped aerogel of claim 12 wherein the inorganic silica-based aerogel is engineered so that at least one of the pores with bonded bioaerosol receptors is sized to allow the targeted bioaerosols to at least partially enter the pores.

19. The bioaerosol receptor doped aerogel of claim 11 wherein the inorganic silica-based aerogel is doped with a single type of bioaerosol receptor.

20. The bioaerosol receptor doped aerogel of claim 11 wherein the inorganic silica-based aerogel is doped with more than one type of bioaerosol receptor.

\* \* \* \* \*

UNITED STATES PATENT AND TRADEMARK OFFICE
CERTIFICATE OF CORRECTION

PATENT NO. : 6,447,991 B1
DATED : September 10, 2002
INVENTOR(S) : Charles E. Daitch et al.

It is certified that error appears in the above-identified patent and that said Letters Patent is hereby corrected as shown below:

Column 9,
Line 17, change "FIG. 1" to -- FIG. 13 --

Signed and Sealed this

Fifteenth Day of April, 2003

JAMES E. ROGAN
*Director of the United States Patent and Trademark Office*